(12) United States Patent
Negiz et al.

(10) Patent No.: US 6,972,348 B2
(45) Date of Patent: Dec. 6, 2005

(54) CATALYTIC CONVERSION OF POLYCYCLIC AROMATICS INTO XYLENES

(75) Inventors: Antoine Negiz, Wilmette, IL (US); Edwin P. Boldingh, Arlington Heights, IL (US); Frank S. Modica, Naperville, IL (US); Gregory F. Maher, Aurora, IL (US)

(73) Assignee: UOP LLC, Des Plaines, IL (US)

( * ) Notice: Subject to any disclaimer, the term of this patent is extended or adjusted under 35 U.S.C. 154(b) by 36 days.

(21) Appl. No.: 10/807,626

(22) Filed: Mar. 24, 2004

(65) Prior Publication Data

US 2005/0215838 A1   Sep. 29, 2005

(51) Int. Cl.$^7$ ............................................. C07C 4/24
(52) U.S. Cl. ..................................................... 585/475
(58) Field of Search ..................................... 585/475

(56) References Cited

U.S. PATENT DOCUMENTS

| | | | |
|---|---|---|---|
| 3,702,886 A | 11/1972 | Argauer et al. ............. | 423/328 |
| 3,709,979 A | 1/1973 | Chu ........................... | 423/328 |
| 3,832,449 A | 8/1974 | Rosinski et al. ............ | 423/328 |
| 3,849,340 A | 11/1974 | Pollitzer ................... | 252/455 Z |
| RE28,341 E | 2/1975 | Wadlinger et al. .......... | 208/120 |
| 4,076,842 A | 2/1978 | Plank et al. ................. | 423/328 |
| 4,159,282 A | 6/1979 | Olson et al. ................ | 585/481 |
| 4,163,018 A | 7/1979 | Tada et al. ................. | 260/429.9 |
| 4,241,036 A | 12/1980 | Flanigen et al. ........... | 423/328 |
| 4,278,565 A | 7/1981 | Chen et al. ............. | 252/455 Z |
| 4,341,914 A | 7/1982 | Berger ........................ | 585/474 |
| 4,440,871 A | 4/1984 | Lok et al. ................... | 502/214 |
| 4,537,754 A | 8/1985 | Casci et al. ................. | 423/277 |
| 4,556,477 A | 12/1985 | Dwyer ....................... | 208/111 |
| 4,567,029 A | 1/1986 | Wilson et al. .............. | 423/306 |
| 4,857,666 A | 8/1989 | Barger et al. ............... | 585/323 |
| 5,296,208 A | 3/1994 | Lesch ......................... | 423/700 |
| 5,723,710 A | 3/1998 | Gajda et al. ................ | 585/467 |
| 5,763,720 A | 6/1998 | Buchanan et al. .......... | 585/475 |
| 5,942,651 A | 8/1999 | Beech, Jr. et al. .......... | 585/475 |
| 5,952,536 A | 9/1999 | Nacamuli et al. .......... | 585/475 |
| 6,060,417 A | 5/2000 | Kato et al. .................... | 502/66 |
| 6,486,372 B1 | 11/2002 | Merlen et al. .............. | 585/467 |
| 6,613,709 B1 | 9/2003 | Merlen et al. ................ | 502/64 |

FOREIGN PATENT DOCUMENTS

EP    0 378 916 A1    12/1989

*Primary Examiner*—Thuan D Dang
(74) *Attorney, Agent, or Firm*—John G. Tolomei; James C. Paschall; Maryann Maas

(57) ABSTRACT

A catalyst, and a process for using the catalyst, that effectively converts and transalkylates indane and $C_{10}$ and heavier polycyclic aromatics into $C_8$ aromatics is herein disclosed. The catalyst comprises a solid-acid support such as mordenite plus a metal component such as rhenium. The catalyst provides excellent conversion of such heavy aromatic species as naphthalene, which is also observed by a decrease in the ending-boiling-point of a hydrocarbon stream passed over the catalyst. The same catalyst is also effective for transalkylation of lighter aromatics, thus yielding a valuable xylenes product stream out of the process.

24 Claims, No Drawings

CATALYTIC CONVERSION OF POLYCYCLIC AROMATICS INTO XYLENES

FIELD OF THE INVENTION

This invention relates to catalytic hydrocarbon conversion, and more specifically to the use of a catalyst for conversion of heavier polycyclic aromatics such as naphthalene and $C_{11}$ aromatics compounds into lighter aromatics such as $C_6$, $C_7$, $C_8$, and $C_9$ aromatics. The catalyst comprises a solid-acid support with a metal hydrogenation component, and the catalyst effectively processes heavy aromatics while also converting lighter aromatics via transalkylation into desirable xylene species.

BACKGROUND OF THE INVENTION

Xylenes isomers, para-xylene, meta-xylene and ortho-xylene, are important intermediates which find wide and varied application in chemical syntheses. Para-xylene upon oxidation yields terephthalic acid, which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomer streams from catalytic reforming or other sources generally do not match demand proportions as chemical intermediates, and further comprise ethylbenzene, which is difficult to separate or to convert. Para-xylene in particular is a major chemical intermediate with rapidly growing demand, but amounts to only 20 to 25% of a typical $C_8$ aromatics stream. Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Often toluene ($C_7$) is dealkylated to produce benzene ($C_6$) or selectively disproportionated to yield benzene and $C_8$ aromatics from which the individual xylene isomers are recovered.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from disproportionation processes often is not sufficiently pure to be competitive in the market. A higher yield of xylenes at the expense of benzene thus is a favorable objective, and processes to transalkylate $C_9$ aromatics and toluene have been commercialized to obtain high xylene yields.

U.S. Pat. No. 4,341,914 discloses a transalkylation process over mordenite using toluene and $C_9^+$ aromatics, where indane is removed as a poison from fresh feed by distillation. U.S. Pat. No. 4,857,666 discloses a transalkylation process over mordenite and suggests modifying the mordenite by steam deactivation or incorporating a metal modifier into the catalyst.

U.S. Pat. No. 5,763,720 discloses a transalkylation process for conversion of $C_9^+$ hydrocarbons into mixed xylenes and $C_{10}^+$ aromatics over a catalyst containing zeolites illustrated in a list including amorphous silica-alumina, MCM-22, ZSM-12, and zeolite beta, where the catalyst further contains a Group VIII metal such as platinum.

U.S. Pat. No. 5,942,651 discloses a transalkylation process in the presence of two zeolite containing catalysts. The first zeolite is selected from the group consisting of MCM-22, PSH-3, SSZ-25, ZSM-12, and zeolite beta. The second zeolite contains ZSM-5, and is used to reduce the level of saturate co-boilers in making a benzene product.

U.S. Pat. No. 5,952,536 discloses a transalkylation process using a catalyst comprising a zeolite selected from the group consisting of SSZ-26, Al-SSZ-33, CIT-1, SSZ-35, and SSZ-44. The catalyst also comprises a mild hydrogenation metal such as nickel or palladium, and can be used to convert aromatics with at least one alkyl group including benzene.

U.S. Pat. No. 6,060,417 discloses a transalkylation process using a catalyst based on mordenite with a particular zeolitic particle diameter and having a feed stream limited to a specific amount of ethyl containing heavy aromatics. The catalyst contains nickel or rhenium metal.

U.S. Pat. No. 6,486,372 B1 discloses a transalkylation process using a catalyst based on dealuminated mordenite with a high silica to alumina ratio that also contains at least one metal component. U.S. Pat. No. 6,613,709 B1 discloses a catalyst for transalkylation comprising zeolite structure type NES and rhenium.

Many types of supports and elements have been disclosed for use as catalysts in processes to transalkylate various types of lighter aromatics into xylenes. However, applicants have found that even heavier polycyclic aromatics can be converted into lighter aromatics and be further converted into xylenes via more conventional transalkylation pathways. Indane and $C_{10}^+$ components, such as naphthalenes, had previously been regarded as coke precursors in conventional transalkylation technologies, but applicants have found a catalyst and a process to convert these components to a great extent, and that permits processing low-value, heavy aromatics into high-value, light aromatics with less stringent feed stream pre-fractionation specifications.

SUMMARY OF THE INVENTION

A principal object of the present invention is to provide a process for the transalkylation of alkylaromatic hydrocarbons. More specifically, the process of the present invention is directed to converting aromatic hydrocarbons with improved conversion of heavy aromatics components such as naphthalene and indane. This invention is based on the discovery that a catalyst based on a solid-acid material in conjunction with a metal component exhibits high effectiveness for conversion when contacted under transalkylation conditions.

Accordingly, a broad embodiment of the present invention is a process for transalkylation of indane and $C_{10}^+$ aromatics to $C_8$ aromatics over a catalyst. The catalyst has a solid-acid component such as mordenite, mazzite, zeolite beta, ZSM-11, ZSM-12, ZSM-22, ZSM-23, MFI topology zeolite, NES topology zeolite, EU-1, MAPO-36, MAPSO-31, SAPO-5, SAPO-11, SAPO-41, and silica-alumina. The catalyst also has a metal component.

In another embodiment, the present invention is a process for conversion and transalkylation of heavy aromatics to xylenes over a solid-acid catalyst with a metal component, where the stream ending-boiling-point over the catalyst is reduced by about 5° C. or more. Effective metal components include, for example, platinum, palladium, nickel, tin, lead, iridium, germanium, and rhenium.

In yet another embodiment, the present invention is a fractionation scheme based upon an apparatus practicing the process of transalkylating heavy aromatics with specifications permitting indanes and naphthalenes to come in contact with a metal stabilized solid-acid catalyst.

These, as well as other objects and embodiments will become evident from the following detailed description of the invention.

DETAILED DESCRIPTION OF THE INVENTION

The feed stream to the present process generally comprises alkylaromatic hydrocarbons of the general formula $C_6H_{(6-n)}R_n$, where n is an integer from 0 to 6 and R is $CH_3$, $C_2H_5$, $C_3H_7$, or $C_4H_9$, in any combination. Suitable alkylaromatic hydrocarbons include, for example but without so limiting the invention, benzene, toluene, ortho-xylene, meta-xylene, para-xylene, ethylbenzene, ethyltoluenes, propylbenzenes, tetramethylbenzenes, ethyl-dimethylbenzenes, diethylbenzenes, methylpropylbenzenes, ethylpropylbenzenes, triethylbenzenes, di-isopropylbenzenes, and mixtures thereof.

The feed stream also comprises naphthalene and other $C_{10}$ and $C_{11}$ aromatics and suitably is derived from one or a variety of sources. Polycyclic aromatics such as the bi-cyclic components including naphthalene, methylnaphthalene, or indane are preferred components for the feed stream of the present invention. Indane, which is also referred to as indan or indene, is meant to define a carbon number nine aromatic species with one carbon six ring and one carbon five ring wherein two carbon atoms are shared. Naphthalene is meant to define a carbon number ten aromatic species with two carbon six rings wherein two carbon atoms are shared. Preferably the polycyclic aromatics are present in amounts above the trace amounts noted in prior art, and these amounts are herein defined as substantial amounts such as greater than about 0.3 wt-% and even more preferably greater than about 0.5 wt-% of the feed stream.

Feed components may be produced synthetically, for example, from naphtha by catalytic reforming or by pyrolysis followed by hydrotreating to yield an aromatics-rich product. The feed stream may be derived from such product with suitable purity by extraction of aromatic hydrocarbons from a mixture of aromatic and nonaromatic hydrocarbons and fractionation of the extract. For instance, aromatics may be recovered from reformate. Reformate may be produced by any of the processes known in the art. The aromatics then may be recovered from reformate with the use of a selective solvent, such as one of the sulfolane type, in a liquid-liquid extraction zone. The recovered aromatics may then be separated into streams having the desired carbon number range by fractionation. When the severity of reforming or pyrolysis is sufficiently high, extraction may be unnecessary and fractionation may be sufficient to prepare the feed stream. Such fractionation typically includes at least one separation column to control feed end point.

The feed heavy-aromatics stream, characterized by $C_9^+$ aromatics (or $A_9^+$), permits effective transalkylation of light aromatics such as benzene and toluene with the heavier $C_9^+$ aromatics to yield additional $C_8$ aromatics that are preferably xylenes. The heavy-aromatics stream preferably comprises at least about 90 wt-% total aromatics, and may be derived from the same or different known refinery and petrochemical processes as the benzene and toluene and/or may be recycled from the separation of the product from transalkylation.

The feed stream is preferably transalkylated in the vapor phase and in the presence of hydrogen. If transalkylated in the liquid phase, then the presence of hydrogen is optional. If present, free hydrogen is associated with the feed stream and recycled hydrocarbons in an amount of from about 0.1 moles per mole of alkylaromatics up to 10 moles per mole of alkylaromatic. This ratio of hydrogen to alkylaromatic is also referred to as hydrogen to hydrocarbon ratio. The transalkylation reaction preferably yields a product having an increased xylene content and also comprises toluene. The conversion of naphthalene over the catalyst is preferably greater than about 80 wt-%, while the conversion of methylnaphthalene is preferably greater than about 75 wt-%. The conversion of indane is preferably greater than about 50 wt-%, and even more preferably greater than about 75 wt-%, all conversions being calculated on a fresh-feed basis.

The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of an effluent stream comprising unconverted feed and product hydrocarbons. This effluent is normally cooled by indirect heat exchange against the stream entering the reaction zone and then further cooled through the use of air or cooling water. The effluent may be passed into a stripping column in which substantially all $C_5$ and lighter hydrocarbons present in the effluent are concentrated into an overhead stream and removed from the process. An aromatics-rich stream is recovered as net stripper bottoms which is referred to herein as the transalkylation effluent.

To effect a transalkylation reaction, the present invention incorporates a transalkylation catalyst in at least one zone, but no limitation is intended in regard to a specific catalyst other than such catalyst must possess a solid-acid component and a metal component. Without wishing to be bound to any one theory, it is believed that such catalyst selectively saturates at least one ring of the polycyclic aromatic compound, cracks that one ring, which results in a remaining single-ring aromatic compound with alkyl groups that is much more resistant towards further saturation than the original polycyclic or multi-ring compound. This remaining alkylated single-ring aromatic compound will readily undergo transalkylation with other single-ring aromatic compounds like benzene or toluene to produce xylenes. Conditions employed in the transalkylation zone normally include a temperature of from about 200° to about 540° C. The transalkylation zone is operated at moderately elevated pressures broadly ranging from about 100 kPa to about 6 MPa absolute. The transalkylation reaction can be effected over a wide range of space velocities. Weighted hourly space velocity (WHSV) is in the range of from about 0.1 to about 20 hr$^{-1}$.

The transalkylation effluent is separated into a light recycle stream, a mixed $C_8$ aromatics product and a heavy recycle stream. The mixed $C_8$ aromatics product can be sent for recovery of para-xylene and other valuable isomers. The light recycle stream may be diverted to other uses such as to benzene and toluene recovery, but alternatively is recycled partially to the transalkylation zone. The heavy recycle stream contains substantially all of the $C_9$ and heavier aromatics and may be partially or totally recycled to the transalkylation reaction zone.

Several types of transalkylation catalysts that may be used in the present invention are based on a solid-acid material combined with a metal component. Suitable solid-acid materials include all forms and types of mordenite, mazzite (omega zeolite), beta zeolite, ZSM-11, ZSM-12, ZSM-22, ZSM-23, MFI type zeolite, NES type zeolite, EU-1, MAPO-36, MAPSO-31, SAPO-5, SAPO-11, SAPO-41, and silica-alumina or ion exchanged versions of such solid-acids. For example, in U.S. Pat. No. 3,849,340 a catalytic composite is described comprising a mordenite component having a $SiO_2/Al_2O_3$ mole ratio of at least 40:1 prepared by acid extracting $Al_2O_3$ from mordenite prepared with an initial $SiO_2/Al_2O_3$ mole ratio of about 12:1 to about 30:1 and a metal component selected from copper, silver and zirconium. Refractory inorganic oxides, combined with the above-mentioned and other known catalytic materials, have been found useful in transalkylation operations. For instance, silica-alumina is described in U.S. Pat. No. 5,763,720. Crystalline aluminosilicates have also been employed in the art as transalkylation catalysts. ZSM-12 is more particularly described in U.S. Pat. No. 3,832,449. Zeolite beta is more particularly described in Re. 28,341 (of original U.S. Pat. No. 3,308,069). A favored form of zeolite beta is described in U.S. Pat. No. 5,723,710, which is incorporated herein by reference. The preparation of MFI topology zeolite is also well known in the art. In one method, the zeolite is prepared by crystallizing a mixture containing an alumina source, a silica source, an alkali metal source, water and an alkyl ammonium compound or its precursor. Further descriptions are in U.S. Pat. No. 4,159,282, U.S. Pat. No. 4,163,018, and U.S. Pat. No. 4,278,565.

Other suitable solid-acid materials include mazzite, ZSM-11, ZSM-22, ZSM-23, NES type zeolite, EU-1, MAPO-36, MAPSO-31, SAPO-5, SAPO-11, SAPO-41. Preferred mazzite zeolites include Zeolite Omega. The synthesis of the Zeolite Omega is described in U.S. Pat. No. 4,241,036. ZSM intermediate pore size zeolites useful in this invention include ZSM-5 (U.S. Pat. No. 3,702,886); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842). European Patent EP 378,916 describes NES type zeolite and a method for preparing NU-87. The EUO structural-type EU-1 zeolite is described in U.S. Pat. No. 4,537,754. MAPO-36 is described in U.S. Pat. No. 4,567,029. MAPSO-31 is described in U.S. Pat. No. 5,296,208 and typical SAPO compositions are described in U.S. Pat. No. 4,440,871 including SAPO-5, SAPO-11, SAPO-41.

A refractory binder or matrix is optionally utilized to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica. Alumina is a preferred binder.

The catalyst also contains an essential metal component. One preferred metal component is a Group VIII (IUPAC8–10) metal, preferably a platinum-group metal. Alternatively a preferred metal component is rhenium. Of the preferred platinum group, i.e., platinum, palladium, rhodium, ruthenium, osmium and iridium, platinum is especially preferred. This component may exist within the final catalytic composite as a compound such as an oxide, sulfide, halide, or oxyhalide, in chemical combination with one or more of the other ingredients of the composite, or, preferably, as an elemental metal. This component may be present in the final catalyst composite in any amount which is catalytically effective, generally comprising about 0.01 to about 2 wt-% of the final catalyst calculated on an elemental basis. The platinum-group metal component may be incorporated into the catalyst in any suitable manner such as coprecipitation or cogellation with the carrier material, ion exchange or impregnation. Impregnation using water-soluble compounds of the metal is preferred. Typical platinum-group compounds which may be employed are chloroplatinic acid, ammonium chloroplatinate, bromoplatinic acid, platinum dichloride, platinum tetrachloride hydrate, tetraamine platinum chloride, tetraamine platinum nitrate, platinum dichlorocarbonyl dichloride, dinitrodiaminoplatinum, palladium chloride, palladium chloride dihydrate, palladium nitrate, etc. Chloroplatinic acid is preferred as a source of the especially preferred platinum component.

Moreover, when the preferred metal component is rhenium, typical rhenium compounds which may be employed include ammonium perrhenate, sodium perrhenate, potassium perrhenate, potassium rhenium oxychloride, potassium hexachlororhenate (IV), rhenium chloride, rhenium heptoxide, and the like compounds. The utilization of an aqueous solution of ammonium perrhenate is highly preferred in the impregnation of the rhenium component. Rhenium may also be used in conjunction with a platinum-group metal. This component may be present in the final catalyst composite in any amount which is catalytically effective, generally comprising about 0.01 to about 2 wt-% of the final catalyst calculated on an elemental basis.

The catalyst may contain additional modifier metal components. Preferred metal components of the catalyst include, for example, tin, germanium, lead, indium, and mixtures thereof. Catalytically effective amounts of such metal modifiers may be incorporated into the catalyst by any means known in the art. A preferred amount is a range of about 0.01 to about 2.0 wt-% on an elemental basis. In summary, the preferred metal components are platinum, palladium, nickel, tin, lead, iridium, germanium, rhenium, or a combination thereof; with platinum-tin or rhenium especially preferred.

EXAMPLES

The following examples are presented only to illustrate certain specific embodiments of the invention, and should not be construed to limit the scope of the invention as set forth in the claims. There are many possible other variations, as those of ordinary skill in the art will recognize, within the scope of the invention.

Example One

Samples of catalysts comprising mordenite were prepared for comparative pilot-plant testing by the forming process called extrusion. Typically, 2500 g of a powder blend of 25 wt-% alumina (commercially available under the trade names Catapal™ B and/or Versal™ 250) and 75 wt-% mordenite (commercially available under the trade name ZeolySt™ CBV-21A) was added to a mixer. A solution was prepared using 10 g nitric acid (67.5 wt-% $HNO_3$) with 220 g deionized water and the solution was stirred. The solution was added to the powder blend in the mixer, and mulled to make dough suitable for extrusion. The dough was extruded through a die plate to form cylindrically shaped (0.16 cm diameter) extrudate particles. The extrudate particles were calcined at about 565° C. with 15 wt-% steam for 2 hours.

Three different catalysts were finished using the extrudate particles and an evaporative impregnation with rhenium metal by using an aqueous solution of ammonium perrhenate ($NH_4ReO_4$). The impregnated base was calcined in air at 540° C. for 2 hours. Catalyst A was finished at 0.7 wt-% rhenium. Catalyst B was finished at 0.15 wt-% rhenium. Catalyst C was finished at 0.4 wt-% rhenium.

A fourth catalyst was prepared on an extrudate particle similar to that used above, but an additional ingredient of MFI zeolite (commercially available as ZSM-5 under the trade name Zeolyst CBV 8014) was used to make a powder blend of 40 wt-% mordenite, 15 wt-% MFI, and 45 wt-% alumina. The extrudate particle, prepared as above, was finished with 0.05 wt-% platinum using chloroplatinic acid and 0.5 wt-% tin using tin chloride. This final catalyst was labeled Catalyst D.

Example Two

Catalysts A, B, C, and D were tested for aromatics transalkylation ability in a pilot plant using a heavy aromatics feed blend to demonstrate effectiveness of indane and naphthalene conversion and selectivity to xylenes. Table 1 provides the feed composition where 5.5 wt-% of the feed contains the coke precursors of indane, naphthalene species, and $C_{11}^+$ aromatics. The test consisted of loading a vertical reactor with catalyst and contacting the feed at 2860 kPa abs (400 psig) under a space velocity (WHSV) of 2 $hr^{-1}$ and hydrogen to hydrocarbon ratio ($H_2$/HC) of 4. Before contacting the catalyst with the feed, the catalyst was reduced using hydrogen at 500° C. Various feed conversion levels were tested by adjusting reactor block temperatures and the results are shown in Tables 2 and 3 for high and moderate conversion of $C_9^+$ material respectively.

The data showed extremely high conversion of coke precursors, which are also called poly-nuclear aromatic species, and these high conversions agree with the drop in the 99.5 wt-% ending-boiling-point across the reactor. The data also showed selective saturation of one of the rings in a polycyclic aromatic based on the showing of selectivity towards benzene and alkybenzenes instead of towards equivalent carbon number paraffinic species. Accordingly, a feed with over 5 wt-% coke precursors, defined as $C_{11}^+$ aromatics plus polycyclic aromatics such as indane and naphthalene species, can be processed successfully in a transalkylation process for xylenes. Such a heavier feed stream permits easier fractionation specifications on distillation equipment used in front of the process, and permits a greater amount of heavy aromatics to be tolerated over the catalyst used in the invention.

TABLE 1

Feed Composition

| Feed Stream Component | Amount (wt-%) |
|---|---|
| Xylenes | 0.1 |
| Tri-methyl-benzene (TMBz) | 45.5 |
| Methyl-ethyl-benzene (MEBz) | 35.0 |
| Propyl-benzene (prop-Bz) | 3.3 |
| C10 Aromatics | 10.6 |
| Indane | 0.5 |
| Naphthalene | 0.6 |
| Methylnaphthalene | 0.8 |
| Ethylnaphthalene | 0.1 |
| Dimethylnaphthalene | 0.6 |
| Trimethylnaphthalene | 0.3 |
| C11+ | 2.6 |
| Total Components | 100 |
| ASTM D-2887 simulated GC method: 99.5 wt-% ending boiling point | 333° C. |

TABLE 2

High $C_9^+$ Conversion

| Catalyst | A | B | C | D |
|---|---|---|---|---|
| $A_9^+$ Conversion | 63.0 | 60.2 | 58.2 | 57.2 |
| Reactor Temp. ° C. | 389 | 420 | 394 | 396 |
| Conversion (wt-%) | | | | |
| TMBz | 47.0 | 45.2 | 41.2 | 37.0 |
| MEBz | 88.6 | 87.4 | 87.0 | 89.7 |
| Prop-BZ | 99.3 | 99.5 | 99.5 | 99.6 |
| C10A | 36.1 | 30.4 | 23.0 | 23.4 |
| Indane | 90.2 | 90.4 | 90.0 | 69.7 |
| Naphthalene | 97.3 | 88.7 | 94.1 | 89.9 |
| Methylnaphthalene | 89.5 | 50.6 | 74.4 | 78.4 |
| Ethylnaphthalene | 84.3 | 53.8 | 70.4 | 74.5 |
| Dimethylnaphthalene | 75.9 | 0.0 | 41.9 | 61.3 |
| Trimethylnaphthalene | 73.0 | 20.7 | 49.2 | 69.2 |
| C11+ | 64.7 | 39.2 | 47.8 | 40.6 |
| 99.5 End Point (° C.) | 273.5 | 297.8 | 309.4 | 290.2 |
| Selectivity (wt-%) | | | | |
| C1 | 10.7 | 5.7 | 7.0 | 0.1 |
| C2 | 12.0 | 17.9 | 13.8 | 19.7 |
| C3 | 7.8 | 9.8 | 6.6 | 7.2 |
| C4 | 4.0 | 2.2 | 2.6 | 3.3 |
| C5 | 1.1 | 0.6 | 0.7 | 1.0 |
| C6 | 0.8 | 0.2 | 0.4 | 0.5 |
| C7 | 0.2 | 0.0 | 0.1 | 0.1 |
| C8 | 0.0 | 0.0 | 0.0 | 0.0 |
| Benzene | 3.2 | 3.5 | 3.2 | 3.7 |
| Toluene | 19.8 | 20.4 | 20.3 | 23.4 |
| Ethylbenzene | 1.2 | 1.4 | 1.5 | 1.1 |
| Xylenes | 39.1 | 38.3 | 43.7 | 39.8 |
| Total | 100.0 | 100.0 | 100.0 | 100.0 |

TABLE 3

Moderate $C_9^+$ Conversion

| Catalyst | A | B | C | D |
|---|---|---|---|---|
| $A_9^+$ Conversion | 49.8 | 42.9 | 47.13935 | 39.5 |
| Reactor Temp. ° C. | 363 | 377 | 374 | 369 |
| Conversion (wt-%) | | | | |
| TMBz | 36.3 | 30.8 | 33.4 | 21.7 |
| MEBz | 74.4 | 67.8 | 74.1 | 70.0 |
| Prop-BZ | 97.3 | 98.0 | 98.2 | 97.5 |
| C10A | 4.7 | 0.0 | 0.0 | 0.0 |
| Indane | 83.2 | 80.0 | 82.7 | 51.5 |
| Naphthalene | 95.3 | 91.1 | 94.4 | 81.8 |
| Methylnaphthalene | 90.7 | 71.3 | 80.7 | 69.3 |
| Ethylnaphthalene | 73.1 | 32.5 | 59.3 | 55.5 |
| Dimethylnaphalene | 75.7 | 27.0 | 51.3 | 50.6 |
| Trimethylnaphalene | 69.1 | 33.7 | 52.5 | 60.0 |
| C11+ | 41.3 | 6.2 | 23.5 | 5.7 |
| 99.5 End Point (° C.) | 278.1 | 294.4 | 292.5 | 319.4 |

TABLE 3-continued

Moderate $C_o^+$ Conversion

| Catalyst | A | B | C | D |
|---|---|---|---|---|
| Selectivity (wt-%) | | | | |
| C1 | 8.9 | 1.1 | 3.8 | 0.1 |
| C2 | 13.0 | 14.3 | 13.4 | 16.6 |
| C3 | 6.9 | 6.7 | 6.2 | 5.7 |
| C4 | 4.3 | 2.2 | 2.7 | 2.3 |
| C5 | 1.7 | 0.6 | 0.8 | 0.8 |
| C6 | 1.6 | 0.3 | 0.7 | 0.5 |
| C7 | 0.9 | 0.1 | 0.3 | 0.2 |
| C8 | 0.3 | 0.0 | 0.0 | 0.0 |
| Benzene | 2.6 | 3.4 | 3.0 | 4.1 |
| Toluene | 17.9 | 21.7 | 20.5 | 28.0 |
| EthylBenzene | 2.4 | 3.6 | 2.9 | 3.0 |
| Xylenes | 39.5 | 43.0 | 44.8 | 37.9 |
| Total | 100.0 | 100.0 | 100.0 | 100.0 |

What is claimed is:

1. A process for transalkylation of aromatics comprising contacting a feed stream comprising naphthalene and $C_{11}$ aromatics with a catalyst at transalkylation conditions to produce a product stream comprising $C_8$ aromatics, the catalyst comprising a solid-acid support material selected from the group consisting of mordenite, mazzite, zeolite beta, ZSM-11, ZSM-12, ZSM-22, ZSM-23, MFI topology zeolite, NES topology zeolite, EU-1, MAPO-36, MAPSO-31, SAPO-5, SAPO-11, SAPO-41, silica-alumina, ion-exchanged version thereof, and mixtures thereof and a metal component selected from the group consisting of platinum, palladium, nickel, tin, lead, iridium, germanium, rhenium, or a combination thereof.

2. The process of claim 1 wherein the solid-acid support material is selected from the group consisting of mordenite, zeolite beta, MFI topology zeolite, silica-alumina and mixtures thereof.

3. The process of claim 2 wherein the solid-acid support material is mordenite and the metal component is selected from the group consisting of platinum, tin, and rhenium.

4. The process of claim 1 wherein the feed stream and product stream are further characterized by having an ending-boiling-point of 99.5 wt-% as determined by the D2887 simulated distillation GC method, and said product stream ending-boiling-point is less than said feed stream ending-boiling-point by at least about 5° C.

5. The process of claim 4 wherein the product stream ending-boiling-point is less than the feed stream ending-boiling-point by at least about 10° C.

6. The process of claim 1 wherein the feed stream naphthalene content is at least about 0.3 wt-%.

7. The process of claim 6 wherein the feed stream naphthalene content is at least about 0.5 wt-%.

8. The process of claim 6 wherein the conversion of feed stream naphthalene is at least about 80 wt-% calculated on a fresh feed basis.

9. The process of claim 1 wherein the transalkylation conditions comprise a temperature from about 200° to about 540° C., a pressure from about 100 kPa to about 6 MPa absolute, and a space velocity from about 0.1 to about 20 $hr^{-1}$.

10. The process of claim 1 wherein the catalyst further comprises an inorganic oxide binder.

11. A process for transalkylation of aromatics comprising contacting a feed stream comprising a substantial amount of indane and naphthalene with a catalyst at transalkylation conditions to produce a product stream comprising $C_8$ aromatics, the catalyst comprising an inorganic oxide binder, a solid-acid material selected from the group consisting of mordenite, mazzite, zeolite beta, ZSM-11, ZSM-12, ZSM-22, ZSM-23, MFI topology zeolite, NES topology zeolite, EU-1, MAPO-36, MAPSO-31, SAPO-5, SAPO-11, SAPO-41, and silica-alumina and mixtures thereof, and a metal component; wherein the product stream ending-boiling-point of 99.5 wt-%, as determined by the D2887 simulated distillation GC method, is less than the feed stream ending-boiling-point by at least about 5° C.

12. The process of claim 11 wherein the feed stream indane content is at least about 0.3 wt-%.

13. The process of claim 12 wherein the feed stream indane content is at least about 0.5 wt-%.

14. The process of claim 11 wherein the metal component is selected from the group consisting of platinum, palladium, nickel, tin, lead, iridium, germanium, rhenium, or a combination thereof.

15. The process of claim 14 wherein the solid-acid material is mordenite and the metal component is rhenium present in an amount about 0.01 to about 2 wt-%.

16. The process of claim 11 wherein the transalkylation conditions comprise a temperature from about 200° to about 540° C., a pressure from about 100 kPa to about 6 MPa absolute, and a space velocity from about 0.1 to about 20 $hr^{-1}$.

17. The process of claim 11 wherein the conversion of feed stream indane is at least about 50 wt-% calculated on a fresh feed basis.

18. The process of claim 17 wherein the conversion of feed stream indane is at least about 75 wt-% calculated on a fresh feed basis.

19. The process of claim 11 wherein the conversion of feed stream naphthalene is at least about 80 wt-% calculated on a fresh feed basis.

20. A process for transalkylation of aromatics comprising contacting a feed stream comprising substantial amounts of indane, naphthalene, and $C_{11}$ aromatics with a catalyst at transalkylation conditions comprising a temperature from about 200° to about 540° C., a pressure from about 100 kPa to about 6 MPa absolute, and a space velocity from about 0.1 to about 20 $hr^{-1}$ to produce a product stream comprising $C_8$ aromatics, the catalyst comprising an inorganic oxide binder, a solid-acid material selected from the group consisting of mordenite, mazzite, zeolite beta, ZSM-1, ZSM-12, ZSM-22, ZSM-23, MFI topology zeolite, NES topology zeolite, EU-1, MAPO-36, MAPSO-31, SAPO-5, SAPO-11, SAPO-41, and silica-alumina and mixtures thereof, and a metal component selected from the group consisting of platinum, palladium, nickel, tin, lead, iridium, germanium, rhenium, or a combination thereof; wherein the product stream ending-boiling-point of 99.5 wt-% as determined by the D2887 simulated distillation GC method is less than the feed stream ending-boiling-point by at least about 5° C., the conversion of feed stream naphthalene is at least about 80 wt-% calculated on a fresh feed basis, and the conversion of feed stream indane is at least about 50 wt-% calculated on a fresh feed basis.

21. The process of claim 20 wherein the total amount of indane and naphthalene is greater than about 0.5 wt-%.

22. The process of claim 20 wherein the conversion of feed stream indane is at least about 75 wt-% calculated on a fresh feed basis.

23. The process of claim 20 wherein the feed stream further comprises methylnaphthalene, and conversion of the feed stream methylnaphthalene is at least about 50 wt-% calculated on a fresh feed basis.

24. The process of claim 20 wherein the product stream ending-boiling-point is less than the feed stream ending-boiling-point by at least about 10° C.

* * * * *

UNITED STATES PATENT AND TRADEMARK OFFICE
CERTIFICATE OF CORRECTION

PATENT NO.   : 6,972,348 B2
DATED        : December 6, 2005
INVENTOR(S)  : Antoine Negiz et al.

It is certified that error appears in the above-identified patent and that said Letters Patent is hereby corrected as shown below:

<u>Column 10,</u>
Line 53, replace "ZSM-1" with -- ZSM-11 --.

Signed and Sealed this

Twenty-eighth Day of March, 2006

JON W. DUDAS
*Director of the United States Patent and Trademark Office*